United States Patent [19]

Spoerke

[11] 3,945,970

[45] Mar. 23, 1976

[54] PREPARATION OF METHACRYLAMIDES

[75] Inventor: Roger W. Spoerke, Akron, Ohio

[73] Assignee: The Goodyear Tire & Rubber Company, Akron, Ohio

[22] Filed: June 28, 1974

[21] Appl. No.: 484,051

[52] U.S. Cl. ....... 260/47 UA; 260/80.3 N; 260/80.7; 260/89.7 R; 260/89.7 N; 260/562 R; 428/462
[51] Int. Cl.². C08F 2/16; C08F 20/58; C08F 20/60
[58] Field of Search ......... 260/80.3 N, 47 UA, 80.7, 260/89.7 N, 89.7 R; 450/632.5

[56] References Cited
UNITED STATES PATENTS 3,767,628   10/1973   Kline .............................. 260/78 UA

*Primary Examiner*—Stanford M. Levin
*Attorney, Agent, or Firm*—F. W. Brunner; J. A. Rozmajzl

[57] ABSTRACT

An improved process for the preparation of methacrylamides from primary amines, methacrylic esters, and base catalysts such as alkoxides and amides. Some products are obtained in the form useful as comonomers in the preparation of elastomers.

12 Claims, No Drawings

PREPARATION OF METHACRYLAMIDES

This invention relates to methacrylamides, to a process for their preparation and to a process for their use as a comonomer in polymerization of elastomers. More particularly, this invention relates to a process for obtaining methacrylamides in good yield and in a form pure enough to be useful as a comonomer in the preparation of elastomers.

Methacrylamides produced by the process of this invention are useful as antioxidant compositions that may be joined to polymeric materials and act as antioxidants not susceptible to normal extraction or volatilization.

Prior methods of preparation of these methacrylamides have involved potentially toxic materials such as acryloyl chlorides and produced undesirable by-products such as hydrochloric acid and sulfur dioxide. Preparations not involving acryloyl chlorides produced methacrylamides in yields and purities that did not lend themselves to commercial applications. It is therefore an object of the present invention to provide an improved process for the production of methacrylamides. Other objects will become apparent to those skilled in this art as the description proceeds.

The process of this invention is carried out by placing a primary amine in a solvent having a boiling point above 100° C., adding a base selected from the group consisting of alkoxides, amides, hydrides, hydroxides and alkali or alkaline earth metals to the solution containing the primary amine, adding a methacylic ester to this mixture and carrying out the reaction at elevated temperatures. The product of the reaction is an intermediate metal salt which is hydrolyzed in an aqueous/acidic media to form the methacrylamide.

Reaction temperature can vary between 50° C. and 250° C. but the normal temperature range is from 65° C. to 200° C. Preferably, temperatures are from 80° C. to 180°C. The time of reaction varies directly with the temperature. Reaction time ranges from 30 minutes to 20 hours but usually ranges from one hour to 16 hours. The preferred reaction time is from 2 hours to 6 hours.

Esters useful in the practice of the present invention are methacrylic esters having the general formula

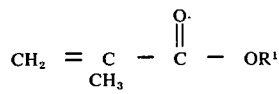

wherein $R^1$ is a radical selected from the group consisting of alkyl radicals having from 1 to 10 carbon atoms, aryl radicals having from 6 to 12 carbon atoms and cycloalkyl radicals having from 5 to 12 carbon atoms.

Amines useful in the present invention are primary, aliphatic or aromatic amines having the general formula

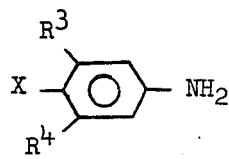

wherein X is selected from the group consisting of $R^2$-NH and OH, $R^2$ is selected from the group consisting of alkyl radicals having from 1 to 20 carbon atoms, cycloalkyl radicals having from 5 to 12 carbon atoms, aryl radicals having from 6 to 12 carbon atoms and aralkyl radicals having from 7 to 13 carbon atoms, $R^3$ and $R^4$ are the same or different radicals selected from the group consisting of hydrogen and tert.alkyl radicals having from 4 to 8 carbon atoms.

Bases useful in the practice of the present invention are those of sufficient strength to abstract a hydrogen from the amine and initiate the formation of an intermediate metallic salt of the structure

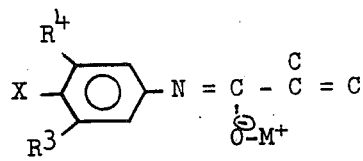

wherein $R^3$, $R^4$ and X are the same radicals as described above and M is a metal selected from the group consisting of lithium, sodium, potassium, and cesium. The bases containing these metals can be hydroxides, alkoxides, hydrides, borohydrides or the metals themselves. The alkoxide bases have the general formula $MOR^5$, wherein $R^5$ is the alkyl radical containing from 1 to 5 carbon atoms.

Other useful alkoxy metal halide bases include those of the general formula $R^5OZX$, wherein $R^5$ is an alkyl radical, Z is an alkaline earth metal selected from the group consisting of magnesium and calcium, and X is a halide selected from the group consisting of chlorine and bromine.

The intermediate metallic salt is hydrolyzed with acid to form methacrylamide having the general structure

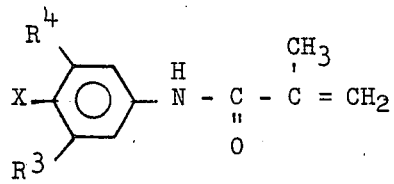

wherein $R^1$, $R^3$ and $R^4$ are the same radicals as described above.

Representative examples of $R^1$, $R^3$ and $R^4$ radicals useful in the structures are alkyl radicals such as methyl, ethyl, t-butyl, octyl, nonadecyl, decyl, tetradecyl and eicodecyl; of aryl radicals are phenyl, benzyl, tolyl, and t-butyl phenyl; of cycloalkyl radicals are cyclopentyl, dicyclohexyl, cyclooctyl and cyclodecyl; and of aralkyl radicals are methyl benzyl, heptyl benzyl, heptyl phenyl, and ethyl phenyl.

Solvents useful in the practice of the present invention are those having a boiling point above 100° C. and not detrimental to the reaction system. Representative examples of such solvents are xylene, isopropyl benzene, chlorobenzene, dichlorobenzene, diisopropyl benzene, naphthalene, anthracene, decalin, kerosene and p-cymene.

Representative examples of bases useful in the practice of the present invention are sodium methoxide, sodium ethoxide, sodium isopropoxide, sodium t-butoxide, potassium methoxide, potassium ethoxide, cesium methoxide, potassium amide, lithium amide, lithium hydroxide, lithium aluminum hydride, methoxy magnesium chloride, ethoxy calcium bromide, n-butoxy magnesium chloride, iso-propoxy calcium bromide, sec-pentoxy calcium chloride, potassium isopropoxide, potassium t-butoxide, lithium methoxide, lithium ethoxide, sodium amide, sodium, potassium, cesium, calcium and magnesium.

Representative examples of esters that can be used in the practice of the present invention are methyl methacrylate, ethyl methacrylate, phenyl methacrylate, t-butyl methacrylate and cyclopentyl methacrylate.

Representative examples of primary amines useful in the practice of the present invention are p-aminodiphenylamine, N-isopropyl-p-phenylenediamine, 2,6-di-t-butyl-4-aminophenol, N-hexyl-p-phenylaminediamine, p-amino-4'-methyl-diphenylamine, p-amino-4'-ethoxy-diphenylamine, p-amino-4'-isopropyl diphenylamine and N-cyclohexyl-p-phenylenediamine.

The synthesis described in this invention comprises mixing approximately equivalent molar amounts of the primary amine and base in a suitable organic solvent. Excess amounts of either amine or base have little effect on the reaction since only 1:1 molar reactions take place. Molar ratios of ester:base:amine are normally from 3:3:1 to 1:1:3 respectively, although molar ratios of ester:base:amine of 1:1:1 respectively are preferred. Any unreacted material is either reused or discarded. The ester is then added slowly. The solution is refluxed, forming an intermediate metallic salt and volatile by-products. The distillate is then discarded. The reaction mixture is cooled and the intermediate metallic salt is removed from solution and washed with an organic solvent such as toluene or xylene until the washed solution is clear. The salt is dried and hydrolyzed in dilute acid to form a solid product. The solid product is then removed from solution and dried at room temperature.

These compounds are useful as antioxidants in elastomers. Simple incorporation into the elastomer by the conventional techniques well known to those of ordinary skill in this art such as by addition to polymer latices or by addition to solid polymers in a Banbury mixer or on a mill can be used. In addition, these compounds, which are made from unsaturated esters, can be copolymerized with conventional monomers used in the preparation of synthetic elastomers. When so copolymerized the products of this process are nonvolatile and not easily extracted.

The invention is more concretely described with reference to the examples below, wherein all parts and percentages are by weight unless otherwise indicated.

EXAMPLE 1

A 1000 cubic centimeter three-necked flask was charged with 500 cubic centimeters of para-xylene. The para-xylene was warmed slightly and agitated. The system was purged with nitrogen to exclude air. Ninety-two grams (0.5 mole) of para-aminodiphenylamine was added to the solvent. The solution was heated to 120° C. with stirring to dissolve the amine. While heating 30 grams (0.52 mole) of sodium methoxide was added. The system was closed by placing a dropping funnel into the third neck of the 1000 milliliter flask. One neck was fitted with a stirring rod and the other formed a take-off for methyl alcohol formed by the abstraction of hydrogen from the amine which recombines with the methoxide and other by-products during reaction. The dropping funnel was charged with 55 cubic centimeters (0.52 mole) of methyl methacrylate. While the solvent was being heated and stirred, the ester was added dropwise slowly until the entire amount was introduced into the system. The methanol product was driven off after being formed along with minor amounts of ester and solvent. The reaction was allowed to run four hours, during which time an intermediate metallic salt formed. The entire system was then cooled to between 60° C. to 65° C. The salt was filtered from the solvent. Washing with 1500 cubic centimeters of para-xylene was necessary to remove unreacted amine. The washings were followed by washings of hexane to expel most of the para-xylene solvent, forming a partially dry salt. The salt was then placed into 1000 cubic centimeters of distilled water and diluted hydrochloric acid was added (50 cubic centimeters concentrated hydrochloric acid and 200 cubic centimeters of water) to reduce the pH to the acid side of 7. The product was then filtered and washed several times with water followed by hexane. The product was dried in a vacuum oven at 65° C. overnight. The N-4-anilinophenyl methacrylamide product yield was 82 grams (65%) having a melting point between 101° C. and 103° C.

EXAMPLES 2 – 7

Examples 2–7 were run in the same manner as shown and described in Example 1. The molar ratio of all reactants was 1.0 mole of amine to 1.1 mole of base to 1.1 mole of ester. The amine in all cases was para-aminodiphenylamine. The base in all cases was sodium methoxide. The ester in all cases was methyl methacrylate. The volume of the various solvents used was 500 cubic centimeters. Benzene is included as a comparative example of a low boiling solvent. The results are shown in Table I.

Table I

| | Effect of Solvent on the Yield of N-4-Anilinophenyl Methacrylamide | | | |
|---|---|---|---|---|
| Ex. | Solvent (b.p. in °C) | Reaction Time (hrs) | Conversion Mole % | Purity Wt % | Yield Mole % |
| 2 | benzene (80) | 12.0 | 61 | 95 | 58 |
| 3 | toluene (110) | 4.5 | 61 | 93 | 57 |
| 4 | p-xylene (138) | 4.0 | 65 | 92 | 60 |
| 5 | p-cymene (176) | 3.0 | 80 | 85 | 68 |
| 6 | kerosene (150–80) | 1.5 | 77 | 80 | 62 |
| 7 | decalin (195) | 3.0 | 87 | 72 | 63 |
| 8 | diisopropyl benzene (210) | 3.0 | 76 | 88 | 67 |

Table I shows that by the use of higher boiling point solvents the yield can be improved by as much as 20 percent and the time of reaction reduced by as much as 95 percent.

In order to avoid loss of expensive starting materials, a system of recycling the unreacted amine was devised. A 0.5 molar charge of p-aminodiphenylamine was made in p-xylene and reacted with equal molar quantities of methyl methacrylate and sodium methoxide. The materials were reacted four hours after which time a sodium salt having the structure (A)

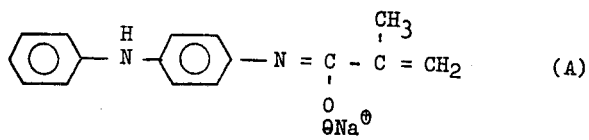

was removed from the solution. The solvent containing unreacted p-aminodiphenylamine was recharged with an additional .35 mole of p-aminodiphenylamine to replace that which had reacted. Equal molar amounts of ester and base were added. The mixture was reacted for an additional four hours. Again, a sodium salt having structure (A) was filtered off. This sequence was repeated twice. Table II shows the results of the recycling of the unreacted p-aminodiphenylamine.

Table II

| Run No. | Moles of Amine Charged | Percent Yield | (based only on amine charged) |
| --- | --- | --- | --- |
| 1 | .5 | 65 | |
| 2 | .35 | 88 | |
| 3 | .35 | 99 | |

As each run concluded, only the reacted amine was replaced. A 65 percent reaction rate per run was assumed, based on the original reaction. Actual yields calculated at the conclusion of the experiments disclosed that more product was obtained than could be produced using only the freshly added amine. The results indicate that some unreacted amine from previous runs remains dissolved in the solvent and subsequently reacted while concentrations of the product were low.

Increasing the reaction temperature increases yields and decreases reaction time. Increasing the reaction temperature is accomplished by using solvents having higher boiling points. Solvents containing unreacted primary amines can be recycled and further utilization of the amine can be realized to minimize the loss of expensive reactant.

The salt formed during the reaction can be copolymerized into elastomers without first hydrolyzing. An "in situ" hydrolysis occurs forming a built-in antioxidant but eliminating the hydrolysis and subsequent separation from solution. The salt can also be washed with water to remove the base from the salt, starting the hydrolysis to the methacrylamide before the copolymerization. The "in situ" hydrolysis is completed in the polymerization reaction which forms the polymer containing the bound antioxidant.

A sample of N-4-anilinophenyl-methacrylamide prepared as described in Example 1 was polymerized according to the following recipe and compared to a sample which was polymerized using the sodium salt of N-4-anilinophenylmethacrylamide. Both samples were polymerized for 16 hours at 15° C. The reaction was shortstopped with sodium dimethyl dithio carbamate. The reaction mixture was poured into excess agitated isopropyl alcohol to coagulate the polymer. Percent conversion to the polymer form was calculated for all samples, based on the weight of the unreacted butadiene.

| | | |
| --- | --- | --- |
| Butadiene | 67.00 | 67.00 |
| Acrylonitrile | 33.00 | 33.00 |
| Water | 190.00 | 190.00 |
| Soap | 2.5 | 2.5 |
| $Na_3PO_4$ | .20 | .20 |
| Versene $Fe_3$ | .0568 | .0568 |
| $Fe_3SO_4 \cdot 7H_2O$ | .0144 | .0144 |
| Sodium formaldehyde sulfoxylate | .0412 | .0412 |
| Sulfate | .5 | .5 |
| Cumene hydroperoxide | .06 | .06 |
| N-4-anilinophenyl methacrylamide | 1.6 | — |
| Sodium salt of N-4-anilinophenyl methacrylamide | — | 1.6 |

Antioxidant studies were then made on the polymer formed. The polymers containing the antioxidant were extracted for 48 hours in methanol to remove any nonbound stabilizer. The oxygen absorptions were carried out by dissolving the extracted antioxidant-containing polymer in benzene to form a cement. The cements were poured onto aluminum foil and dried to form a thin film. The weight of each sample was determined. The aluminum foil with the adhering rubber sample was placed in the oxygen absorption apparatus and the time required to absorb one percent oxygen by weight was recorded. The testing procedure is fully detailed in Industrial and Engineering Chemistry, 43, page 456 (1951) and Industrial and Engineering Chemistry, 45, page 392 (1953). A control sample containing no methacrylamide absorbed one percent oxygen in less than 10 hours. The results are shown in Table III.

Table III

| | A | B |
| --- | --- | --- |
| Percent conversion to polymer | 85 | 86 |
| Parts of amide built into rubber | .97 | .94 |
| Hours to absorb 1% $O_2$ at 100° C. | 487 | 411 |

A - N-4-anilinophenyl methacrylamide
B - Sodium salt of N-4-anilinophenyl methacrylamide The ionic salt of the amine antioxidant was thus utilized in copolymerization without subsequent hydrolysis eliminating a procedural step. This method was effective both when unreacted base has been removed by water washing, during which an "in situ" hydrolysis occurs, and when the base is present with the salt during copolymerization. The salt was collected and washed after the reaction. It was then added to water to reduce the sodium methoxide to sodium hydroxide base and methanol. The base and methanol were removed with the water from the salt by filtration. The salt was dried in a vacuum oven.

The salt need not be entirely dry before use as a comonomer. The salt may be damp but excessive wetness should be avoided.

Two samples of metallic salts prepared as described in Example 1 can be copolymerized using the same recipe and reaction conditions described above. One sample is washed using p-xylene and then water washed and hydrolyzed. The second sample is not water washed after the p-xylene wash and is used in the polymerization along with any remaining base. Percent conversion to polymer is calculated based on the weight of butadiene remaining. The polymerization containing the washed sample will show about 86 percent conversion to polymer. The polymerization containing the unwashed sample will also show about 86 percent conversion to polymer. Complete removal of the base is not necessary to effect polymerization.

While certain representative embodiments and details have been shown for the purpose of illustrating the invention, it will be apparent to those skilled in this art that various changes and modifications may be made therein without departing from the spirit or scope of the invention.

I claim:
1. A process for the production of a polymer containing a bound methacrylamide antioxidant comprising (a) reacting a methacrylic ester with an amine in an organic solvent having a boiling point above 100° C. in the presence of a basic metallic catalyst to yield an intermediate metallic salt, (b) removing the salt from solution, (c) washing the salt with an organic solvent, (d) at least partially drying the salt, and (e) adding the salt as a comonomer to an aqueous polymerization system wherein an in situ hydrolysis occurs during the polymerization reaction and wherein the methacrylic ester has the general structure (I)

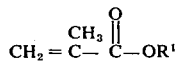    (I), the amine has the general structure (II)

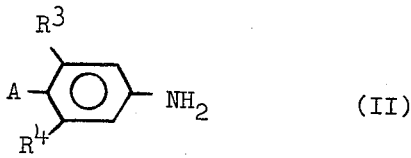    (II)

and the basic metallic catalyst is selected from the group consisting of alkoxy metal halide bases having the formula $R^5OZX$, alkali metals, alkaline earth metals and amides, hydrides, hydroxides and alkoxides of alkali metals and alkaline earth metals, and wherein $R^1$ is a radical selected from the group consisting of alkyl radicals having from 1 to 10 carbon atoms, aryl radicals having from 6 to 12 carbon atoms, cycloalkyl radicals having from 5 to 12 carbon atoms, A is selected from the group consisting of HO— and $R^2$ NH wherein $R^2$ is selected from the group consisting of hydrogen, alkyl radicals having from 1 to 20 carbon atoms, cycloalkyl radicals having from 5 to 12 carbon atoms, aryl radicals having from 6 to 12 carbon atoms, aralkyl radicals having from 7 to 13 carbon atoms and wherein $R^3$ and $R^4$ are the same or different radicals selected from the group consisting of hydrogen and tert. alkyl radicals having from 4 to 8 carbon atoms and wherein $R^5$ is an alkyl radical, Z is an alkaline earth metal selected from the group consisting of magnesium and calcium, and X is a halide selected from the group consisting of chlorine and bromine.

2. A process as described in claim 1 wherein the methacrylic ester starting materials are selected from the group consisting of methyl methacrylate, ethyl methacrylate, t-butyl methacrylate and phenyl methacrylate.

3. A process as described in claim 1 wherein the amine is selected from the group consisting of p-aminodiphenylamine, 2,6-di-t-butyl-4-aminophenol, N-cyclohexyl-p-phenylenediamine, p-amino-4'-methyldiphenylamine, p-amino-4'-ethoxydiphenylamine, N-isopropyl-p-phenylenediamine and methoxydiphenylamine.

4. A process as described in claim 1 wherein the ester/amine reaction takes place in the presence of a basic catalyst selected from the group consisting of sodium methoxide, potassium methoxide, potassium tert.butoxide, lithium methoxide and cesium methoxide.

5. A process as described in claim 1 wherein the ester/amine reaction is carried out in an organic solvent selected from the group consisting of xylene, decalin, isopropyl benzene, chloro benzene, dichloro benzene, diisopropyl benzene, anthracene, naphthalene and kerosene.

6. A process as described in claim 1 wherein the basic metallic catalyst is an alkali metal amide selected from the group consisting of sodium amide, potassium amide and lithium amide.

7. A process as described in claim 1 wherein the basic metallic catalyst is an alkali metal selected from the group consisting of lithium, sodium, potassium and cesium.

8. A process as described in claim 1 wherein the basic metallic catalyst is a borohydride selected from the group consisting of lithium borohydride, sodium borohydride and potassium borohydride.

9. A process as described in claim 1 wherein the basic metallic catalyst is a hydroxide selected from the group consisting of potassium hydroxide, sodium hydroxide, lithium hydroxide and cesium hydroxide.

10. A process as described in claim 1 wherein the basic metallic catalyst is an alkaline earth metal selected from the group consisting of calcium and magnesium.

11. A process as described in claim 1 wherein the basic metallic catalyst is an aluminum hydride selected from the group consisting of lithium aluminum hydride, sodium aluminum hydride, potassium aluminum hydride and cesium aluminum hydride.

12. A process as described in claim 1 wherein the basic metallic catalyst is an alkoxy metal halide of the general formula $R^5OZX$, wherein $R^5$ is an alkyl radical having from 1 to 5 carbon atoms, Z is an alkaline earth metal selected from the group consisting of magnesium and calcium, and X is a halide selected from the group consisting of chlorine and bromine.

* * * * *